United States Patent
Bonnet et al.

(10) Patent No.: US 6,184,172 B1
(45) Date of Patent: Feb. 6, 2001

(54) MIXED FLUORINATION CATALYST

(75) Inventors: Philippe Bonnet; Eric Jorda, both of Lyons; Eric Lacroix, Ambérieux d'Azergues, all of (FR)

(73) Assignee: Elf Atochem S.A., Puteaux (FR)

(*) Notice: Under 35 U.S.C. 154(b), the term of this patent shall be extended for 0 days.

(21) Appl. No.: 09/195,455

(22) Filed: Nov. 18, 1998

(30) Foreign Application Priority Data

Nov. 20, 1997 (FR) .................................... 97 14564

(51) Int. Cl.[7] .................... B01J 27/132; B01J 27/128; B01J 27/125
(52) U.S. Cl. .................... 502/228; 502/224; 502/229; 502/305; 502/313; 502/314; 502/315; 502/319; 502/320; 502/231
(58) Field of Search .................... 502/224, 228, 502/229, 231, 305, 313, 314, 315, 319, 320

(56) References Cited

U.S. PATENT DOCUMENTS 5,523,500 * 6/1996 Cheminal et al. .................... 502/315
5,616,820    4/1997 Cheminal et al. .
5,731,481    3/1998 Cheminal et al. .

FOREIGN PATENT DOCUMENTS

| 486333 | 5/1992 | (EP) . |
| 609123 | 8/1994 | (EP) . |
| 2669022 | 11/1990 | (FR) . |
| 466202 | 12/1975 | (SU) . |

OTHER PUBLICATIONS

French Search Report dated Aug. 13, 1998.

* cited by examiner

Primary Examiner—Elizabeth D. Wood
(74) Attorney, Agent, or Firm—Smith, Gambrell & Russell, LLP

(57) ABSTRACT

Mixed fluorination catalyst comprising one or more nickel and chromium oxides, halides and/or oxyhalides deposited on a support composed of aluminium fluoride or of a mixture of aluminium fluoride and alumina, characterized in that the weight of nickel/weight of chromium ratio is between 0.08 and 0.25, preferably between 0.1 and 0.2.

5 Claims, No Drawings

//MIXED FLUORINATION CATALYST

FIELD OF THE INVENTION

The subject-matter of the present invention is a mixed fluorination catalyst based on nickel and chromium. It also relates to a process for the fluorination of halogenated hydrocarbons in the gas phase by means of hydrofluoric acid (HF) employing the said catalyst.

BACKGROUND OF THE INVENTION

The catalytic fluorination of halogenated hydrocarbons in the gas phase by HF is a well-known method of access to fluorinated hydrocarbons and in particular to hydrofluorocarbons (HFC). The latter are currently used as substitutes for chlorofluorocarbons (CFC), which are suspected of contributing to the weakening of the stratospheric ozone layer.

French Patent Application FR 2,669,022 thus makes known a mixed catalyst composed of nickel and chromium oxides, halides and/or oxyhalides deposited on a support composed of aluminium fluoride or of a mixture of aluminium fluoride and alumina.

The content by weight of nickel and chromium mentioned for the said catalyst is between 0.5 and 20% for each metal, the nickel/chromium atomic ratio being between 0.5 and 5. This catalyst is used for the preparation of 1,1,1,2-tetrafluoroethane (also known as F134a) from 1-chloro-2,2,2-trifluoroethane (F133a). F134a is an HFC, used in particular for refrigeration and freezing, which has no harmful effect on the stratospheric ozone layer.

Application FR 2,669,022 mentions maintenance of the effectiveness over time of the catalyst for a duration ranging up to approximately 400 hours of operation.

However, it is highly desirable to have available a catalyst which, under the conditions for the industrial production of fluorinated hydrocarbons, retains its activity over an operating period of several thousand hours.

The increase in the lifetime of the catalyst for such operating periods is all the more desirable since the decrease in activity, when it occurs, cannot be put right by an in situ regeneration treatment but then requires the shutdown of the production unit in order to replace the charge of the catalyst.

A catalyst which makes it possible to decrease the number of shutdowns of the production unit and which makes it possible, for a given charge of the said catalyst, to produce a greater amount of desired final product is particularly advantageous with respect to the running of the production unit and the cost price of the desired final product.

DESCRIPTION OF THE INVENTION

One aim of the invention is to provide a mixed fluorination catalyst based on nickel and on chromium which retains its activity over an operating period of several thousand hours.

Another aim of the invention is to provide a catalyst which makes it possible to carry out fluorination reactions at a higher temperature.

Another aim of the invention is to provide a fluorination catalyst for which the charge, in the industrial reactor, has to be replaced less frequently.

Another aim of the invention is to provide a more economical process for the fluorination of halogenated hydrocarbons.

Another aim of the invention is to provide a process for the manufacture of 1,1,1,2-tetra-fluoroethane (F134a) which exhibits a high degree of conversion and a high selectivity.

It has now been found that these aims can be achieved, in all or in part, by means of the fluorination catalyst and process described below.

The subject-matter of the present invention is thus, firstly, a mixed fluorination catalyst comprising one or more nickel and chromium oxides, halides and/or oxyhalides deposited on a support composed of aluminium fluoride or of a mixture of aluminium fluoride and alumina, characterized in that the weight of nickel/weight of chromium ratio is between 0.08 and 0.25, preferably between 0.1 and 0.2. The said fluorination catalyst has a lifetime which, surprisingly, is very much improved with respect to that of the catalyst taught by Patent FR 2,669,022.

The catalyst according to the invention can contain, by weight, from 0.1 to 6% of nickel salts and from 1 to 20% of chromium salts, preferably from 0.35 to 4.5% of nickel salts and from 3 to 16% of chromium salts and, more preferably still, from 1 to 2% and from 6 to 12% respectively.

The percentages indicated above are percentages by weight, expressed in the form of the equivalent weight of metal. Unless otherwise mentioned, all the percentages relating to the composition of the catalyst according to the invention are percentages by weight.

Use is preferably made, as chromium and nickel salts, of chlorides but it is also possible to employ other salts, such as, for example, oxalates, formates, acetates, nitrates and sulphates or nickel dichromate, provided that these salts are soluble in the amount of water which can be absorbed by the support.

The catalyst according to the invention can be prepared in a way known per se from an alumina. The latter can, in a first stage, be converted into aluminium fluoride or into a mixture of aluminium fluoride and alumina by fluorination using air and hydrofluoric acid, the degree of conversion of the alumina to aluminium fluoride depending essentially on the temperature at which the fluorination of the alumina is carried out (generally between 200 and 4500° C., preferably between 250 and 400° C.) . The support is subsequently impregnated using aqueous solutions of chromium trioxide, of nickel salt and of an agent which reduces the chromium, such as methanol.

When chromium trioxide ($CrO_3$) is used as precursor of the chromium, this chromium can be reduced by any means known to the person skilled in the art (chemical reducing agent, thermal reduction, and the like), provided that the technique used does not harm the properties of the catalyst and thus its activity. The preferred chemical reducing agent is methanol.

The catalyst according to the invention can also be prepared by direct impregnation of the alumina using solutions of the abovementioned chromium and nickel compounds. In this case, the conversion of at least a portion (70% or more) of the alumina to aluminium fluoride is carried out during the stage of activation of the catalyst, generally carried out before it is employed.

The aluminas which can be used and which are defined below for the preparation of the catalyst according to the present invention are well-known products which are commercially available. They are generally prepared by calcination of hydrated aluminas at a temperature of between 300 and 800° C. and can comprise high contents (up to 1000 ppm) of sodium, without this harming the catalytic performance.

Before it is employed, the catalyst according to the invention has to be conditioned, that is to say converted into constituents which are active and stable (to the reaction conditions) by a prior so-called activation operation.

This treatment can be carried out either "in situ" (in the fluorination reactor) or else in appropriate equipment designed to withstand the activation conditions. The activation generally comprises one or more of the following stages:

low-temperature drying (100 to 250° C., preferably 110 to 200° C.) in the presence of air or of nitrogen, high-temperature drying (250 to 450° C., preferably 300 to 350° C.) under nitrogen or under air, low-temperature fluorination (180 to 300° C., preferably at approximately 200° C.) by means of a mixture of hydrofluoric acid and of nitrogen, the content of HF being controlled so that the temperature does not exceed 350° C., and finishing under a stream of pure hydrofluoric acid or of hydrofluoric acid diluted with nitrogen at a temperature which can range up to 450° C.

During this operation, the catalytic precursors (nickel and chromium halides, chromate, nickel dichromate, chromium oxide) are converted into corresponding fluorides and/or oxyfluorides, which results in water and/or hydrochloric acid being given off.

This activation also contributes to increasing the fluorination of the alumina, when the impregnation has been carried out on an already partially fluorinated support, or, when the alumina is directly impregnated, to the fluorination of the latter. In the latter case, it is necessary to exert perfect control over the temperature (the fluorination of the alumina is highly exothermic), if it is not desired to harm the physical characteristics of the catalyst; furthermore, the amounts of water generated are markedly greater.

Chemical analysis of the elements (chromium, nickel, fluorine, aluminium, oxygen) after activation makes it possible to confirm the inorganic composition of the catalyst according to the invention.

The activated form of the catalyst is, in the same way as the unactivated form, included in the catalyst which is the subject-matter of the present invention.

The lifetime which is desirable for the catalyst according to the invention is evaluated according to the test described below.

Test of the Lifetime of the Catalyst:

A-Ageing test on the catalyst 5 ml of activated catalyst, according to the invention, are charged to a tubular reactor with an internal diameter of 27 mm made of Inconel 600 (alloy comprising nickel, chromium and iron in respective proportions of 75%, 15% and 8% by weight). This catalyst is subsequently brought to a temperature of 490° C. while being maintained under an $N_2$/HF (50 mol %/50 mol %) flow of 1 mol of mixture per hour.

When a temperature of 490° C. is reached, the catalyst is then subjected to an HF flow of 1 mol/hour containing 1 mol % of $O_2$ for 24 hours.

This accelerated ageing test is representative of the operating conditions for a fluorination catalyst during several thousand hours.

B-Performance of the catalyst

The performance of the catalyst is evaluated before and after the accelerated ageing test in the following way.

This performance is tested by the ability to catalyse the fluorination of F133a to F134a by the action of HF and is represented by the degree of conversion of the F133a.

The operating conditions of this reaction are as follows:

catalyst volume: 5 ml in a tubular reactor identical to that used above;

temperature: 350° C.

pressure: atmospheric contact time: 0.5

HF/F133a molar ratio: 4 duration: 24 hours.

C-Lifetime of the catalyst

This is thus assessed by the difference in the degrees of conversion of the F133a recorded in the presence of the catalyst before and after the ageing test, in accordance with the operating conditions described above.

Under the conditions of this test, it is considered that a difference of less than 3% indicates that the lifetime of the catalyst is, under industrial conditions, several thousand hours.

Another subject-matter of the invention is a process for the fluorination of halogenated hydrocarbons in the gas phase by means of hydrofluoric acid employing the catalyst according to the invention.

The process according to the invention is suitable for both saturated and unsaturated halogenated hydrocarbons and in particular olefinic halogenated hydrocarbons. It is particularly well suited to the manufacture of fluorinated hydrocarbons comprising from 1 to 3 carbon atoms and 1 or more hydrogen atoms. Mention may be made, without implied limitation, as examples of starting halogenated hydrocarbons, of the following compounds: $CHCl_3$, $CCl_2=CHCl$, $CHCl_2-CClF_2$, $CH_2Cl-CF_3$, $CH_3-CCl_2-CH_3$, $CCl_3-CF_2-CH_3$, $CCl_3-CF_2-CHCl_2$, $CCl_3-CF_2-CH_2Cl$, $CHCl_2-CHCl-CH_3$, $CH_2Cl-CHCl-CH_3$, $CCl_2=CCl_2$, as well as $CF_3-CH=CHF$, $CH_2Cl_2$, $CH_2ClF$, $CCl_2=CH-CCl_2H$, $CCl_3-CH=CHCl$, $CHCl_2-CCl_2F$, $CHCl_2-CF_3$, $CHFCl-CF_3$, $CH_2Cl_2$, $CH_2ClF$, $CHF_2Cl$ or $CHFCl_2$.

It is preferable to employ the process according to the invention for the preparation of 1,1,1,2-tetrafluoroethane (F134a) from 1-chloro-2,2,2-trifluoroethane (F133a). The use of the catalyst according to the invention makes it more convenient to operate the industrial plant and in particular introduces the possibility of occasionally setting a higher temperature. In this case, an advantageously high selectivity for F134a is also obtained.

The temperature of the fluorination reaction is generally between 50 and 500° C., depending on the starting materials and the fluorinated hydrocarbon desired. It is preferable to operate between 300 and 500° C. when it is desired to substitute all the chlorine atoms by fluorine atoms.

The contact time, defined as being the ratio of the "volume of the catalyst" to the "total flow rate of the reactants" (measured under the reaction conditions) can vary within wide limits and is generally between 3 and 100 seconds. In practice, it is preferable to operate with contact times of between 5 and 30 seconds, so as to obtain both an advantageously high degree of conversion and an advantageously high productivity.

The HF/starting halogenated hydrocarbon molar ratio also varies within wide limits, depending in particular on the nature of this hydrocarbon and the stoichiometry of the reaction. It is generally between 1 and 20, preferably between 2 and 10.

The operating pressure is between 1 and 20 bar absolute (0.1 to 2 MPa), preferably between 5 and 16 bar.

The catalyst according to the invention can operate as a stationary bed or as a fluidized bed. The stationary bed is preferred when the reaction is not exothermic.

According to a preferred alternative form of the process of the invention, the fluorination reaction is carried out in the presence of oxygen. It is preferable to use an "$O_2$/starting halogenated hydrocarbon" ratio of between 0.001 and 10, preferably between 0.5 and 5 (mol %). The introduction of oxygen advantageously makes it possible to restore the activity of the catalyst when the activity occasionally decreases because of the deposition, on its surface, of products such as coke.

EXAMPLES

The following examples illustrate the invention and can under no circumstances be interpreted as a limitation of the latter.

Example 1

A-Preparation of the catalyst 300 ml of $AlF_3$, obtained by fluorination of alumina in a fluidized bed at approximately 300° C. using air and hydrofluoric acid (concentration by volume of 5 to 10% of this acid in the air), are placed in a rotary evaporator. The starting alumina exhibits the following physicochemical characteristics:

shape: beads with a diameter of 1–2 mm;

BET specific surface: 223 m$^2$/g pore volume: 1.2 cm$^3$/g (for pore radii of between 40 Å and 63 microns);

sodium content: 900 ppm.

Furthermore, two separate aqueous solutions are prepared:

a chromium trioxide ($CrO_3$) solution to which nickel chloride hexahydrate has been added;

a methanolic solution containing 3 to 4.5 molar equivalents of methanol per mole of chromium.

The mixture of these two solutions is subsequently introduced at ambient temperature, at atmospheric pressure and over approximately 45 minutes, onto $AlF_3$ with stirring. The amounts of chromium and nickel salts are adjusted in order to obtain the desired molar equivalents of Cr and Ni in the catalyst which are indicated in the following table.

B-Activation.

5 ml of the catalyst prepared previously are charged to a tubular reactor with an internal diameter of 27 mm made of Inconel 600. Drying is carried out at 200° C. under a nitrogen stream for 4 hours.

The catalyst is subsequently gradually fluorinated by introduction of an $HF/N_2$ (50 mol %/50 mol %) mixture and by bringing (over 5 hours) the temperature from 200° C. to 350° C., the latter being maintained for 8 hours. The activation stage is terminated by treatment with pure HF at 350° C. for 10 hours.

These catalysts are subsequently subjected to the lifetime test defined previously. The result of this test is indicated in the table in the form of the degree of conversion of the F133a before and after accelerated ageing (expressed as mol %)

The degrees of conversion and the selectivities are also expressed in the present text in mol %.

| Catalyst | % Ni | % Cr | Ni/Cr Ratio | Degree of conversion of the F133a | |
|---|---|---|---|---|---|
| | | | | before accelerated ageing | after accelerated ageing |
| A | 1 | 6 | 0.17 | 10.2 | 11.3 |
| B | 1 | 9 | 0.11 | 15.6 | 12.7 |
| C | 1.5 | 9 | 0.17 | 9.1 | 10.4 |
| D | 2 | 9 | 0.22 | 13.1 | 10 |
| E | 2 | 12 | 0.17 | 13.5 | 12.3 |

These results show that for the catalysts A to E according to the invention, the decrease in the degree of conversion of the F133a after the ageing test is limited to a maximum of 3%. Such a behaviour indicates, for these catalysts, a lifetime of several thousand hours under the operating conditions of an industrial fluorination unit.

Example 2

Fluorination of F133a to F134a.

The performances of the catalysts of Example 1 were tested (after activation) under the following operating conditions:

catalyst volume (in bulk): 75 ml temperature: 350° C.

pressure: atmospheric flow rate of hydrofluoric acid: 1.09 mol/h flow rate of F133a: 0.26 mol/h that is to say, an HF/F133a molar ratio of 4.2 and a contact time of 3.9 seconds under the reaction conditions.

The gases resulting from the reaction are freed from hydracids by washing with water and are then dried and analysed by vapour phase chromatography.

A degree of conversion of the F133a of 21%, a selectivity of 99% and an F134a productivity of 75 g/h/l are obtained.

Example 3

Example 2 is repeated, 1% (in moles) of $O_2$ with respect to the F133a also being introduced into the reaction mixture.

After operating for 1000 hours, a degree of conversion of the F133a of greater than 20% and an F134a selectivity and productivity greater than 97% and 60 g/h/l respectively are observed.

Example 4

Example 2 is repeated, 1.5% (in moles) of $O_2$ with respect to the F133a being introduced into the reaction mixture and the reaction being carried out at a temperature of 420° C. and a pressure of 15 bar absolute. The flow rate of the reactants is as follows:

flow rate of HF : 2.15 mol/hour flow rate of F133a: 1.08 mol/hour i.e. an HF/F133a molar ratio equal to 2 and a contact time of 22 seconds.

A degree of conversion of the F133a of approximately 22% and an F134a selectivity and productivity of greater than 90% and 290 g/h/l respectively are observed.

Comparative Example

Example 1 is repeated, an Ni/Cr catalyst on an $AlF_3$ support comprising 6% of nickel and 6% of chromium being prepared. A degree of conversion of the F133a before ageing of 12.8% is obtained, which falls to 3.2% after the ageing test.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. Mixed fluorination catalyst comprising at least one nickel oxide and at least one chromium oxide, halide and/or oxhalide deposited on a support composed of aluminum fluoride or of a mixture of aluminum fluoride and alumina, the weight of nickel/weight of chromium ratio is between 0.08 and 0.25.

2. Catalyst according to claim 1, wherein it contains, by weight, from 0.1 to 6% of nickel and from 1 to 20% of chromium.

3. Mixed fluorination catalyst according to claim 1, wherein the ratio is between 0.1 and 0.2.

4. Mixed fluorination catalyst according to claim 2, wherein the weight of nickel is from 0.35 to 4.5% and of chromium is from 3 to 16%.

5. Mixed fluorination catalyst according to claim 2, wherein the weight of nickel is from 1 to 2% and of chromium is from 6 to 12%.

* * * * *